United States Patent [19]

Shofner et al.

[11] 4,396,286

[45] Aug. 2, 1983

[54] ELECTRO-OPTICAL SYSTEM AND METHOD AND APPARATUS FOR PROVIDING AUTOMATICALLY-COMPENSATING, TRACEABLE CALIBRATION AND ZEROING FOR LIGHT SCATTERING DEVICES

[75] Inventors: Frederick M. Shofner; Arthur C. Miller, Jr.; Gerhard Kreikebaum, all of Knoxville, Tenn.

[73] Assignee: PPM, Incorporated, Knoxville, Tenn.

[21] Appl. No.: 146,124

[22] Filed: May 2, 1980

Related U.S. Application Data

[62] Division of Ser. No. 902,510, May 3, 1978, Pat. No. 4,249,244.

[51] Int. Cl.$^3$ ................................................ G01J 1/02
[52] U.S. Cl. ...................................... 356/243; 356/338
[58] Field of Search ............... 356/336, 338, 339, 340, 356/341, 342, 343, 243; 350/315

[56] References Cited

U.S. PATENT DOCUMENTS

| | | | |
|---|---|---|---|
| 2,877,453 | 3/1959 | Mendenhall, Jr. | 356/338 X |
| 3,127,464 | 3/1964 | Gustavson | 356/339 X |
| 3,416,864 | 12/1968 | Keahl et al. | 350/315 X |
| 3,619,037 | 11/1971 | Pugh, Jr. | 350/275 X |
| 3,647,300 | 3/1972 | Skala | 356/343 X |
| 4,013,953 | 3/1977 | Skala | 324/140 R X |
| 4,019,811 | 4/1977 | Lorah et al. | 350/274 |

OTHER PUBLICATIONS

Kirsh et al., "Improvement and Calibration of an AZ Jet–Type Photoelectric Aerosol Counter", *Kolloidnyi Zhurnal,* vol. 37, No. 4, pp. 778–781, 8/1975.

Masucha et al., "Cylindrical Chopper Suitable for use with Vacuum Monochromator", *Science of Light,* vol. 19, No. 1, pp. 26–42, 1970.

*Primary Examiner*—John K. Corbin
*Assistant Examiner*—Matthew W. Koren
*Attorney, Agent, or Firm*—Kerkam, Stowell, Kondracki & Clarke

[57] ABSTRACT

A calibration/zero control is combined with an electro-optical measurement instrument in a time-multiplex fashion to provide a self-diagnostic in situ measurement system and automatic compensation of the entire electro-optical train without interruption of the measurement process. The electro-optical instrument includes a laser which provides a source of substantially monochromatic electromagnetic radiation (laser beam) and optics for collection and focusing radiation onto a detector. The radiation is directed through a sampling volume where it impinges upon an object whose properties or physical characteristics are to be measured by scattering techniques. The calibration/zero control includes an element rotatably positioned in the path of the electromagnetic radiation, optically upstream of the sampling volume, in having an axis of rotation perpendicular to the optical axis such that the radiation is periodically blocked and sampled. The laser source is synchronously pulsed to fire in accordance with the position of the calibration/zero element. The calibration/zero element is constructed such that in one blocking position, a predetermined fraction of the laser beam is allowed to penetrate and pass through the element to the collection optics and detector. The analog voltage of the detector is time-multiplexed to develop diagnostic information including a calibration signal, a zero radiation signal and a measurement signal. All signals are developed under the control of a timing signal derived from the calibration/zero control.

11 Claims, 12 Drawing Figures a) CAL, $\phi = 0$ b) SIGNAL 1, $\phi = 90°$ c) ZERO, $\phi = 180°$ d) SIGNAL 2, $\phi = 270°$

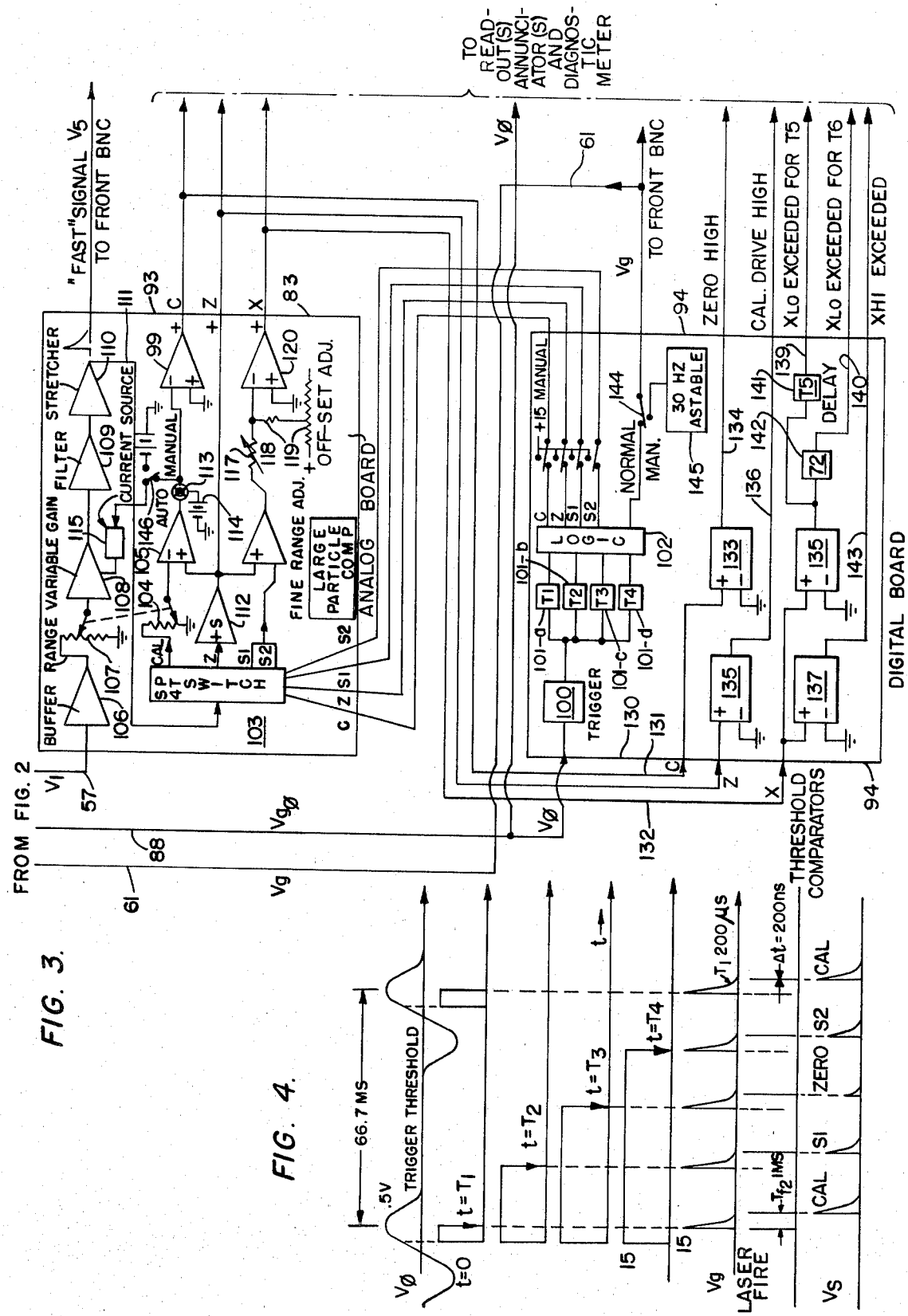

RESPONSE PER UNIT MASS OF ABSORBING PARTICLE DISTRIBUTIONS VERSUS PARTICLE DIAMETERS, FOR ABSORPTION INDICES $A_2 = 0$, 0.1, 0.3, 1.96 FOR FORWARD SCATTERING

ELECTRO-OPTICAL SYSTEM AND METHOD AND APPARATUS FOR PROVIDING AUTOMATICALLY-COMPENSATING, TRACEABLE CALIBRATION AND ZEROING FOR LIGHT SCATTERING DEVICES

This is a division; of application Ser. No. 902,510 filed May 3, 1978, now U.S. Pat. No. 4,249,244.

BACKGROUND OF THE INVENTION

1. Field of the Invention

This invention relates generally to electro-optical measurement of physical properties and more particularly to a method and apparatus for self-diagnosis and automatic compensation of the entire electro-optical instruments particularly adapted for continuous in situ measurement properties of materials, such as for example, the mass per unit volume of particulates or aerosols entrained in a gaseous medium.

The invention is particularly adapted for use in connection with electro-optical methods and systems for making in situ particle measurements of the type described in U.S. Pat. Nos. 3,797,937 and 4,017,186 and the subject matter of the latter patents is hereby incorporated by reference. Reference is also made to the Instructional Manual of the Model C20 Particulate Monitor of PPM Inc. which illustrates and describes an embodiment of the invention in connection with the continuous in situ measurement of oil particulates entrained in a cryogenic process helium flow. The subject matter of the latter instruction Manual is hereby incorporated by reference.

2. Description of the Prior Art

One of the oldest and most widely used electro-optical devices is the optical transmissometer. In recent years, its principal application has been monitoring the opacity of stack emissions. A well-known example is monitoring the effluent of electric generating facilities wherein particulates resulting from combustion of coal or oil are emitted up the stack and into the ambient environment. Under restricted conditions, the opacity, or better the optical density, may be roughly correlated with the mass concentration of particulates in the stack gases. Thus, higher opacity or optical density indicates larger emission levels. Currently, in many countries, including the U.S., regulations are written to limit either (or both) the opacity or the mass emission rates.

Transmissometers operate by transmitting a more or less collimated beam of electromagnetic radiation (usually visible or "photoptic" light) across the stack and measuring the degree of attenuation thereof. In some instruments, the beam is reflected by a mirror system on the opposite side of the stack from the source, back into the source unit, thus permitting a double pass and, more practically, permitting incorporation of both source and receiver beams in the same package. Some instruments permit automatic compensation of the apparatus, but not of the entire electro-optics train and not without interrupting data acquisition.

There are several thousand transmissometers currently in use for opacity monitoring. Clearly, the quality of and the confidence in the measurements could be greatly enhanced if means were available to readily trace the calibration of the instruments to a central, industry-accepted, facility. Still further, superior measurements not now possible would be realized if data were not lost during the calibration cycle.

Another form of electro-optical instrument useful for measuring particulate concentrations is a nephelometer. U.S. Pat. No. 3,563,661 to Charlson and Alhquist describes an integrating nephelometer, which also is a light scattering device. This apparatus measures primarily the scattering coefficient which is related to optical visibility effects in the earth's atmosphere. Visibility reductions result from increasing aerosol concentrations in the atmosphere and are very sensitive to the aerosol particle size, in fact, more so that to the mass concentration of the particles. These devices are calibrated by simulation in the laboratory with known aerosols or by Rayleigh scattering from known gases. Such devices have found limited application because they require relatively sophisticated and highly trained personnel for operation. The calibration obviously requires interruption of data collection and may not be directly traced, being on an individual instrument basis.

In U.S. Pat. No. 3,782,824 to Stoliar and Brown, there is disclosed an apparatus and method for measuring the extinction coefficient of an atmospheric scattering medium using the so-called LIDAR or laser backscattering technique. Again, this electro-optical method yields a property of the earth's atmosphere relating to visibility effects. Whereas the aforementioned integrating nephelometer of Charlson and Alhquist measures light scatter integrated over essentially the zero to 180° angular range and within a small length of space internal to the instrument, the backscatter technique of Stoliar and Brown collects backscattered light within a very small angular range near 180°, over a large region (length along beam) of space. The amplitude of the backscattered yield is related through well-known equations in the art to the properties of aerosols illuminated by the pulsed laser beam. However, the general use of the technique is on a relative indicating basis and absolute calibration is virtually impossible. As with the integrating nephelometer, some attempts have been made to correlate backscattering yield with mass concentration of the aerosols. In certain circumstances this correlation is a fairly satisfactory indicator, but the calibration is not traceable and does not automatically compensate the measurement apparatus.

The aforementioned U.S. Pat. No. 3,797,937 of Shofner describes a system for making particle measurements by forward scattering of laser light. Specifically, the measurements are for the size distribution of relatively large droplets and the apparatus employs an external in situ, sampling volume. No provision is made for either automatic or traceable calibration.

The more recent U.S. Pat. No. 4,017,188 of Shofner and Kreikebaum, describes in electro-optical method and system for in situ measurements of particulate mass density using backscattered LED light. This patent discloses that, under certain circumstances, the backscattered signal correlates well with mass concentration (not mass density as specified in the title) of particulates entrained in a gaseous medium. This patent also discloses a means by which this particular system may be calibrated relatively in the field by insertion of a "standard scattering medium" into the beam. Calibration is achieved by interruption of the measurement process through use of a remotely positioned scattering plate which is brought into position after the sensing head is withdrawn partially from its housing. No provision is made for automatic calibration/zero compensation or for providing traceable calibration information.

Definition of Traceability

When reference is made herein to traceable calibration information, it should be understood to mean that each instrument's calibration is traceable to a laboratory wherein process conditions can be accurately simulated. Traceability means, in the present invention, that the sensitivity of electro-optical instrumentation is tied directly to a stable and precise and simple element of the system which may be readily installed and transported for calibration checks. This means that the optical instrumentation does not have to be transported or even removed from the plant or factory, but, rather, only the calibration elements may be shipped back and forth to the laboratory environment where the accuracy and operability of the instrumentation can be accurately simulated. Extensive, redundant measurements, often tedious gravimetric measurements for particulate analysis, are in such laboratory environments much more easily and accurately executed. For example, traceability of the calibration of a mass concentration monitor might proceed as follows. It would be operated on particles over a wide range of mass concentrations and with roughly similar particulate characteristics as used in the field. The readings of the instrument, with similar optical design, would then be made directly in terms of a calibration element associated with each instrument which introduces a known fraction of light into the collection optics system. If all instruments in the field are of similar optical configuration to the master unit in the calibration facility, then those units' response is uniquely tied to the C/Z element fractional yield, which is uniquely and absolutely connected to the response of the master unit. Traceability thus means that the calibration elements are secondary standards whose signal value is connected to the master instrument and calibration facility. The primary standard then becomes the auxiliary means by which the master instrument is calibrated. Again, for mass concentration measurements as an example, these commonly reduce to various types of gravimetric methods, whereby representative samples of air are pulled through a filter, upon which the particulates are deposited and then their incremental weight is determined. The primary standards thus become that of mass and gas volume analysis, both of which may be traced, through well-known laboratory instrumentation, to the National Bureau of Standards. Thus, the importance of combining the calibration element with a preferred optical system should be readily appreciated.

OBJECTIVES OF THE INVENTION

Accordingly, it is a principal object of the present invention to adapt the concept of traceable calibration element to an automatically compensating electro-optical measurement instrument.

Another object of the present invention is to provide electro-optical instrumentation which enables particulate mass concentration measurements in the order of 1 microgram per cubic meter, and even less, to be made with reliability and confidence.

Still another object of the present invention is to provide a continuous electro-optical sensor and aerosol monitoring system suitable for monitoring particulates of a wide variety of sizes. For purposes of this invention, large particulates are defined as those which are essentially non-respirable, i.e. having a diameter of $d \gtrsim 3$ $\mu$m. Small or fine particulates, on the other hand, are particulates having a diameter which fall in the range of 0.3 $\mu$m. $\lesssim d \lesssim 3$ $\mu$m.

A further object of the invention is to provide a self-diagnostic and automatically compensating electro-optical system and apparatus which includes a traceable calibration/zero element and which responds to particle mass concentration, independently of particle size distribution, shape and especially composition, over wide practical ranges.

It will be readily apparent to those skilled in the art that the realization of the aforementioned objectives by the present invention overcome the disadvantages and limitations of prior art systems and provides many desirable features. For example, the system, method and apparatus of the present invention permit improved accuracy of measurement for light scattering instruments wherein electromagnetic radiation is impinged upon and collected from objects of interest and have application in a variety of environments such as, for example, measurement of properties of natural and man made fibers, either singly or in a plurality; measurement of mass per unit volume of particulate or aerosols entrained in a gaseous medium; continuous dust monitoring in textile mills; continuous acid mist monitoring and monitoring of air quality and the like. The foregoing examples are given by way of illustration and not by way of limitation.

Another feature of the present invention is that it overcomes the disadvantage of "research oriented" electro-optical instrumentation with its requisite sophistication required in personnel operating the equipment and interpreting the data. Another feature of the present invention is that it avoids variability in readings which originate with system gain changes and zero baseline changes. Often these changes are associated with something as simple as contamination of an optical window or lens. Other causes of these variabilities are temperature, humidity, and pressure sensitivities of various electro-optical components such as lasers, LEDs, incandescent bulbs, detectors, pre-amplifiers, integrated circuits, etc. These problems are avoided by providing automatic compensation of the entire electro-optical train and a traceable calibration/zero element as part of the system.

A traceable calibration element means that an instrument in a distant plant may be calibrated, absolutely and accurately, simply by interchanging calibration elements and comparing readings between the plant instrument and a similar "master" instrument maintained in a geographically centrally located calibration facility. Accuracies and confidence levels heretofore impossible may be realized easily and inexpensively and neither sophisticated, "research-type" personnel nor expensive equipment are required. Further, difficult time consuming and error-prone gravimetric measurements methods which require the tedious collection and analysis of particulate matter by mechanical means can be avoided.

SUMMARY OF THE INVENTION

The present invention provides high quality, absolutely accurate, traceable electro-optical system and apparatus which provides automatic calibration and zeroing of the entire electro-optical train, without interruption of data. Calibration and compensation for zero shifts, over a wide dynamic range is done continuously and automatically. A traceable calibration element permits fast and easy evaluation against a fixed standard or "master". Measurements of particle mass concentration may be made independently of particle size distribution, shape and composition cover wide practical ranges.

To this end, in accordance with the present invention, there is provided an electro-optical instrument including a laser source for directing substantially monochromatic electromagnetic radiation through a sampling-volume. Radiation scattered from the surface of an object in the sample volume whose physical characteristics are being monitored is periodically interrupted is collected and focused into a radiation detector. Interruption and sampling of the laser beam is effected by means of calibration/zero assembly including a calibration/zero element which is rotatably positioned to alternately pass and interrupt the laser radiation. The calibration/zero element supports oppositely disposed beam blocking filters which block the main laser beam at the 90° and 270° position of the calibration/zero element but which allow the signal photons from the sampling volume in the angular cone of scattered radiation to pass to the collection optics relatively uninterrupted. Calibration is effected at the zero (0°) position of the calibration/zero element where a constant fraction of the laser beam is collected while signal photons from the sampling volume are blocked. To this end, the calibration/zero element includes a diffuser element positioned to intercept the laser beam and being connected to a plurality of fiber optics to redirect a predetermined fraction of the laser beam radiation to the collection optics. In the case of forward scatter optical instruments, the radiation is directed through the element downstream to the collection optics. In the case of a back-scattered optical instrument, the radiation is directed to the upstream collection optics, i.e. the sampled fraction of radiation exits from thesame face of the calibration/zero element through which it entered. The 180° position of the calibration/zero element establishes a zero reference by blocking signal photons, as well as the main beam. Firing of the laser is synchronized to the four positions of the calibration/zero element by means of a magnetic pick-up device mounted to the rotatably driven calibration/zero element supporting shelf.

BRIEF DESCRIPTION OF THE DRAWINGS

The features of the present invention and the attendant advantages will be readily apparent to those having ordinary skill in the art and the invention will be more easily understood from the following detailed description of the preferred embodiments of the present invention taken in conjunction with the accompanying drawings wherein like reference characters represent like parts throughout the several views.

For an elucidating example, the invention will be described by way of application of the method to a forward scattering system which measures the mass per unit volume of particulates (or aerosols) entrained in a gaseous medium. This example is chosen because it manifests the applicability of the invention in generating reliable information on air quality and also because it affords a relatively simple way of explaining the invention. However, those skilled in the art will readily recognize that the calibration/zeroing means are equally well applicable to backward scattering systems and to other light scattering measurements such as size or surface area distributions of particles entrained in fluid media, diameters of cylindrical objects such as natural and man-made fibers and the measurement of respirable aerosols or dusts.

FIG. 3 is a block diagram of the electronic control circuits of the present invention as applied to the system of FIG. 1;

FIG. 4 is a timing diagram showing the relationships of various pulses developed in the control circuits of the present invention;

FIG. 5 is a diagrammatic illustration of the various positions of the calibration/zero element relevant to obtaining measurement and sampling data broken down into four figures.

DESCRIPTION OF THE PREFERRED EMBODIMENTS

Figure 1:
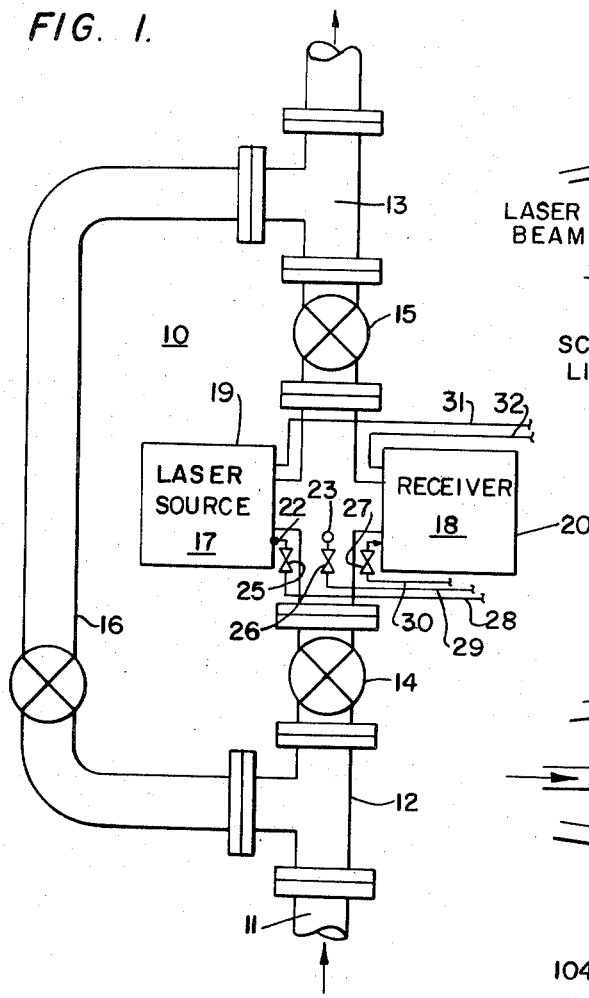
FIG. 1 shows the general configuration of an oil aerosol monitor according to the invention in a high pressure, helium cryogenic process.

The invention may be beneficially incorporated into a wide variety of electro-optical instruments, more particularly light scattering instruments and systems and FIG. 1 shows the general configuration and location of the sensor unit in connection with a forward scattering oil aerosol monitoring system 10 with the scattering volume in situ to a high pressure helium, cryogenic process. The purpose of this instrument is to monitor very low mass concentrations of residual oil aerosols not removed by several stages of control equipment. This application was the first to receive beneficial use of our invention and was first publicly described in the technical paper "A New Laser Aerosol Detector and Monitor for Use on High Pressure Gas Streams," W. E. Harrison, Jr., Frederick M. Shofner, and Arther C. Miller, Jr., presented at the 1977 Cryogenic Engineering Conference, Aug. 2-5, 1977, Boulder, Colo., the subject matter of which is hereby incorporated by reference.

Process helium flow enters the system from the left hand side of the drawing through pipe 11. The main flow pipe 11 is conveniently interrupted by T junctions 12 and 13 which permit monitoring system 10 to be connected to the process flow through valves 14 and 15. T junctions 12 and 13 are interconnected through valved by-pass 16 which enables the process to continue should instrument removal be necessary. The monitor system 10 includes laser source 17 and receiver 18 suitably supported in housing or shells 19 and 20, respectively. Shells 19 and 20 are connected to the flow process through piping 21 when valves 14 and 15 are opened. To permit the shells 19, 20 and connector pipe 21 to be brought up to pressure prior to opening of valves 14 and 15, a plurality of vacuum pumpout ports 22, 23, 24 are provided, each being individually valved as indicated at 25, 26, 27, respectively, and connected to a source of He, not shown, through conduits 28, 29, 30.

Monitoring instrument 10 measures, in situ and continuously, the presence of oil particulates entrained in the cryogenic process helium flow through pipe 11. As will be hereinafter described, the instrument uses forward scattering of laser light and accomplishes high sensitivity and stability through the electro-optical system design which incorporates a calibration/zero system 40 shown in FIG. 2, which permits automatic and continuous compensation for unavoidable changes in transfer gain and baseline zero; both of these variations characteristically limit the application of electro-optical transducer means in making accurate measurement and/or providing process control.

The principle parameters affecting the electro-optical system are:

Gas—He
Pressure—15 atmospheres (=220 psia)
Temperature—Room (=70° F.)
Gas Flow—130 grams/sec (at 15 atm.)
Particulates—Oil aerosols with bulk of mass assumed between roughtly 0.2 and 5 $\mu$m, $\rho=0.98$ g/cm$^3$, high viscosity, low volatility.
Particulate Mass Concentration— <10 ppb or $\chi<2-4<\mu g/m^3$.

The parameter $\chi$ is a direct measure of the particulate matter transported by the process flow and is independent of gas pressure, velocity, temperature, and composition.

Figure 5A:
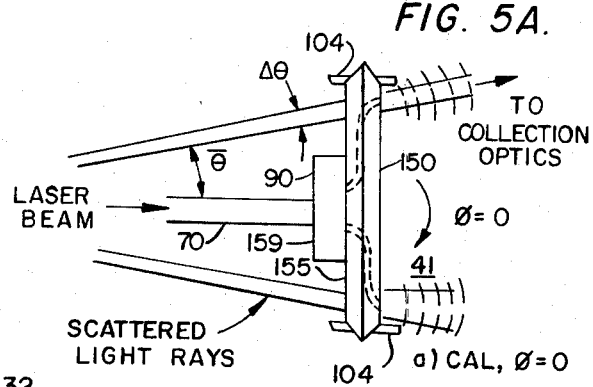
FIG. 5A, FIG. 5B, FIG. 5C and FIG. 5D representing four positions of the rotatable calibration/zero element.
Figure 5B:
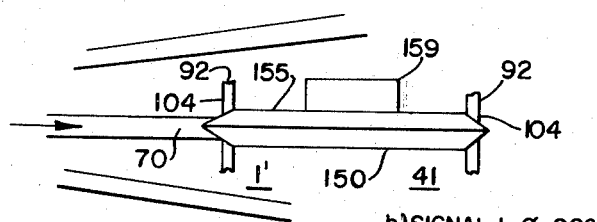
Figure 5C:
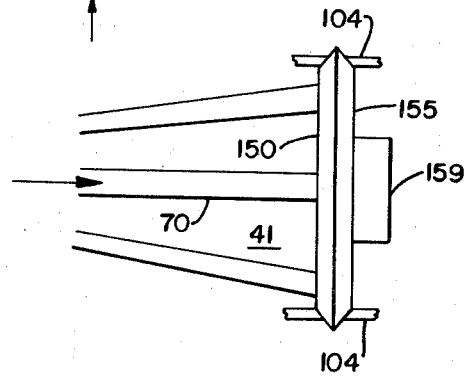
Figure 5D:
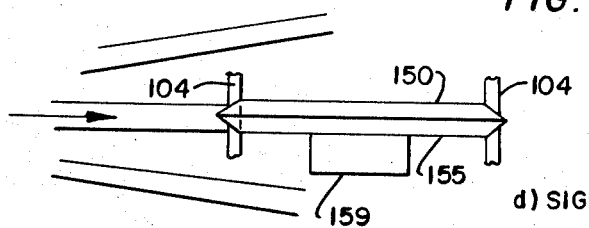

In order to rely upon the output signal as truly representative of the process, the instrument's transfer function must be stable and independent of laser power, lens cleanliness, minor optical misalignments, detector gain, amplifier gain and drifts, etc. If the transfer function is not within tolerance the instrument annuciates and alerts the process operator. This self diagnosis is achieved through operation of the calibration/zero system and the positioning of the calibration/zero element 41 between the sampling volume 42 and the collection optics 43. Referring to FIG. 5, it will be seen that as element 41 is rotated continuously, signals are developed at four positions of the element. FIG. 5A represents the calibrate or "cal" position. In the "cal" position, an optical signal is produced which is directly proportional to total electro-optical transfer gain (from laser power through photon reception and detection through electronic amplification and processing). This signal is compared to a known or set-point signal and the gain control element is so driven by the error signal as to maintain the correct transfer function. FIGS. 5B and 5D represent the normal or signal positions. In each of these positions the signal photons scattered from the sampling volume 42 are passed to the collection optics. In the "zero" position, scattered photons from the sample volume 42 and the main beam are blocked by the C/Z element and a signal is produced corresponding to no scattered light. This signal may be subtracted, via differential amplifiers, both from "cal" and "signal" values to derive the cal signal C and output signal X, as will be hereinafter described.

Figure 2:
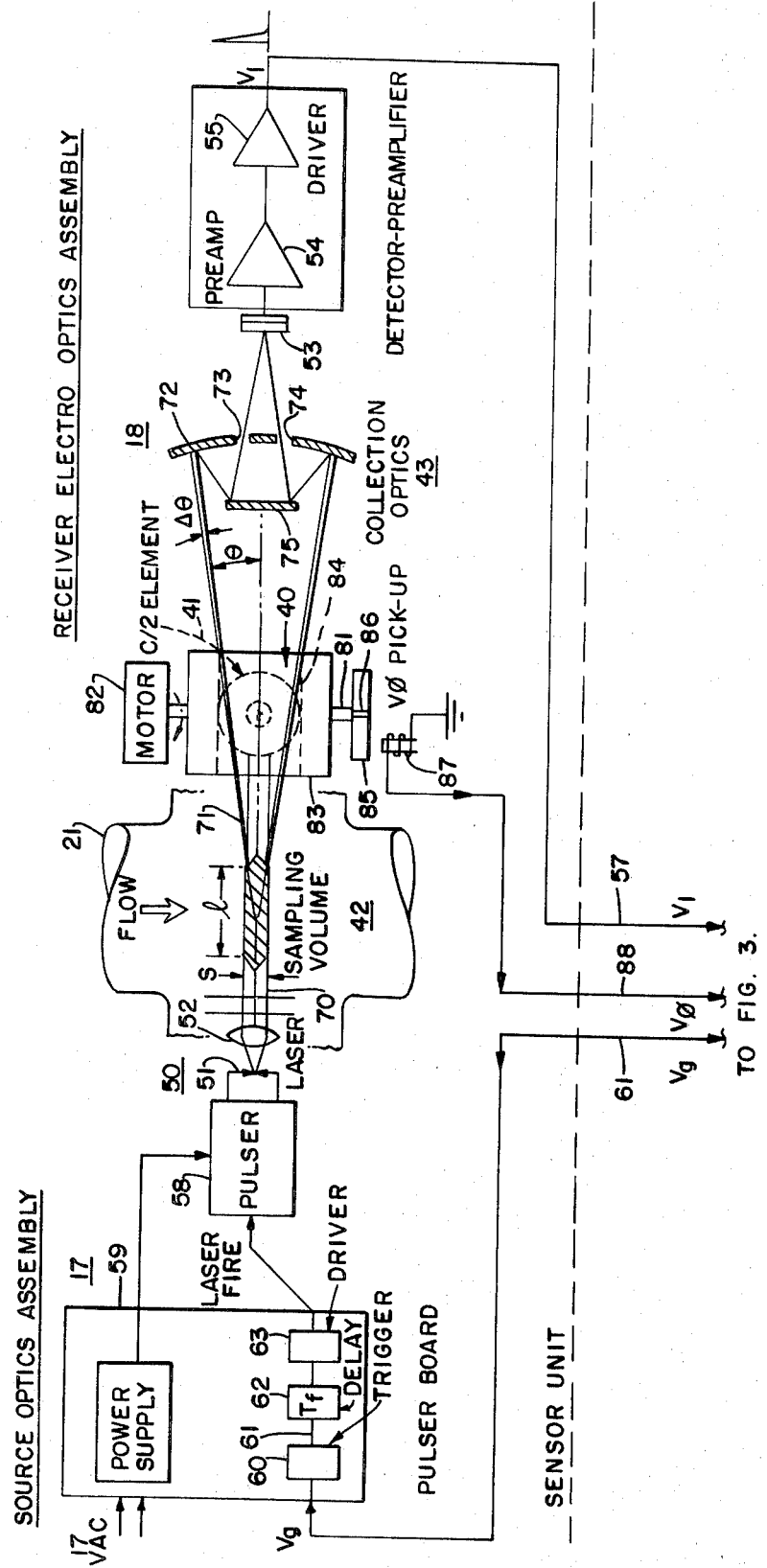
FIG. 2 is a diagrammatic fragmentary and block diagram illustration of the electro-optics of the present invention as applied to the monitor system of FIG. 1.

FIGS. 2 and 3 illustrate the systems electro-optical block diagram. For simplicity, the figures have been broken down into the sensor unit shown in FIG. 2 and the control/read out circuits shown in FIG. 3. Several active and passive elements have been lumped into single blocks and multiple signal sense changes have been omitted to promote clarity of functional operation; however, a complete detailed illustration of the specific circuit arrangements and component deisgnation may be had by reference to applicants' aforementioned instructional manual for the model C20 particulate monitor.

With reference to FIG. 2, the depicted system includes a laser light source 50 which may be a light emitting diode 51, with optical means 52 for directing light from source 50 into the process flow fluid diagrammatically represented by the directional arrow in duct 21. Collection optics 43 are providing for collecting and focusing light forward scattered from the sampling volume 42 onto a light detector 53 which may be a low noice PIN silicon photodiode. Detector 53 converts the light signal into a low level dc analog signal which is applied to a low noise, charge sensitive preamplifier stage 54. The output of the preamplifier stage is applied to a further drive stage 55 via conductor 56. Output of stage 55 is represented as signal V1 which is applied to the control and read out circuits of FIG. 3 via cable 57.

Laser source 50 is pulsed by a conventional laser pulse diode (PTI Model IL6) 58 driven by the output derived from the printed circuit pulser board 59 under control of a gating pulse $V_g$ applied to the trigger 60 via conductor 61. The pulser causes the laser to be fired after an adjustable delay derived through delay stage 62 $T_f$ connected to the input of driver stage 63 which generates the proper firing signal for pulser 58. The source optics assembly board also contains a suitable power supply which converts the 17 VAC input into proper DC operating voltages for the integrated circuits on the board and pulser 58.

It will be understood that the cross sectional geometry of the laser output beam 70 from the laser 50 may be of any of several selected geometries, but preferably is of circular cross section. Where this output beam intercepts the projected acceptance cone 71 of the detector, there is a volume defined as the scattering or sampling volume 42. It is noted that in FIG. 2, only two dimensions S and 1 of the sampling volume are depicted, but it will be recognized that the laser beam is interrupted by the acceptance cone, and consequently the sampling volume usually are each three-dimensional. For present purposes, this sampling volume refers to the volume within which a particle must be located in order for radiation from the laser to impinge on the particle and for the radiation scattered by the particle to be directed in a direction suitable for entry into the detector 53.

In the depicted system, the projected acceptance cone 71 of the photodetector 53 is established through the use of a modified Cassegranian lens 43 comprising concave mirror 72 including apertures 73 and 74. Disposed forwardly of mirror 72 in the direction of the laser source is flat mirror 75. The spatial location with respect to each other of elements 72 and 75 and to the laser beam and photodetector, along with the size of their openings 73 and 74, establish the size of the projected acceptance cone of the photodetector.

In accordance with recognized technology, disregarding for the moment the operation of this calibration/zero system, the radiation emitted from the laser and impinging upon one or more particles within the scattering volume is scattered by the respective particles in all directions. A portion of the scattered radiation from each particle is directed from the scattering volume toward the detector along a path which falls within the projected acceptance cone of the detector.

Such radiation is reflected by mirrors 72 and 75 and passes through the apertures 73 and 74 to be received by the photodetector 53. Also in accordance with known technology, the intensity of the radiation by the photodetector from a particle is a measure of the size of the particle. Within the photodetector, the scattered radiation received by the photodetector from each particle is converted to an electrical signal whose magnitude is uniquely related to the intensity of the radiation scattered from the particle and therefore, to the particle properties, e.g., size. Accordingly, evaluation of the electrical signal developed within the photodetector and fed therefrom as an output signal provides a measure of the particle size. Further, analysis of all of the signals from the detector provides information regarding the size distribution and concentration of the particles within the medium.

It is recognized that when employing a pulsed laser, as will be discussed hereinafter, each time the laser pulses there is a sampling of a known volume of a particle-containing medium, such volume being equal to the sampling volume of the system. From a knowledge of this sampling volume and the number of laser pulses, along with the obtained knowledge of the particle size of each particle detected and measured during a given number of laser pulses, the total number of particles per unit of volume of the particle-containing medium can be obtained as well as a determination of the size distribution of the measured particles within the particle-containing medium.

In the disclosed system, the scattering volume is located internally of the apparatus employed. That is, the scattering volume is not exposed to ambient atmosphere, but rather is in a confined atmosphere, i.e. the sampling volume is disposed within the medium which carries the particles. Particles are measured in situ. However, the sampling volume may be external to the system as shown, for example, in the aforementioned U.S. Pat. No. 3,793,397. It should also be noted that the disclosed system relates to a forward scattering assembly; however, the principle of the invention can equally well be applied to back scatter systems.

The foregoing analysis has been given with respect to conventional electro-optical systems which are readily adopted to include the novel calibration/zero system 40 which forms the basis of the present invention. Referring to FIG. 2, the calibration/zero system includes a C/Z element 41 rotably supported on shaft 81 adapted to be driven by a synchronous hysteresis motor 82. Shaft 81 extends through a supporting A1 motor block 83 having a central aperture 84 dimensioned to permit unrestricted passage of radiation within the limits of the projected acceptance cone and free rotation of the C/Z element 41. Opposite motor 82, shaft 81 supports a magnetic pick-up sensor comprising A1 disc 85 having a magnet 86 thereon positioned to establish a reference position $\Phi$ with respect to the C/Z element. As shown in FIG. 5A, $\Phi = 0$ corresponds to the position where the C/Z element intercepts and blocks the radiation beam, but allows a fixed or constant fraction of the laser beam to be collected and redirected to the collection optics. The reference position $\phi$ is determined by the output $V_\phi$ derived from pick-up coil 87 which causes a pulse $V_\phi$ to be generated on line 88 each time the magnet 86 is driven past the coil. In the system disclosed, the calibration/zero system elements are conveniently housed in receiver shell 20.

Before proceeding with a description of the control circuit of FIG. 3 and the details of construction of the C/Z element, a broad functional overview of the operation of the system will be given. At the sensor unit, shown in FIG. 2, the basic act of transduction takes plce. Oil particulates entrained in the helium flow are impinged upon by radiation beam 70 and scatter light into the collection optics 43. The collection optics selects only that light within a small angular range $\Delta\theta$ and "focuses" it onto detector 53. The photons are then converted by detector 53 and associated preamplifier 54 and driver stage 55 into a voltage pulse whose amplitude $V_1$ is proportional to the mass of particulates in the sampling volume provided their diameters d lie in the range $0.3 \lesssim d \lesssim 3$ $\mu$m. For larger particles which lie in the range of $d > 3$ $\mu$m, the range of response to mass concentration may be electronically extended. The laser 50 is fired in synchronism with the position of the calibration zero element 41 driven by motor 82. The laser 50 is caused to be fired four times per revolution of the C/Z element 41, at equally spaced intervals, and the point in space at which the laser fires is set by the $V_\phi$ pick-up voltage derived from pick-up coil 87.

As shown in FIG. 2, the laser beam 70 and receiver optical axes pass through the axis of rotation of the C/Z element 41. These two axes are perpendicular to each other. Referring now to FIG. 5A, in the CAL position, $\phi = 0$, a constant fraction of the laser beam is collected by the C/Z element and redirected into the collection optics which define the mean angle and angular range of light collection, $\theta$ and $\Delta\theta$. Signal photons in the angular range of light collection $\Delta\theta$ from the sampling volume are blocked in this position by the peripheral radial portions of the C/Z detector. A known fraction of the laser beam power is passed through an attenuator 90 and connecting fiber optics 91 to the face of the C/Z element away from the laser source 50.

It should be apparent, however, in the case of a backscattered element, the C/Z assembly would be positioned between the laser source and the sampling volume in which case the fraction of laser beam radiation collected would be redirected in the direction of backscattered radiation, i.e. the direction from whence it came.

Upon 90° rotation of the C/Z element, FIG. 5B-$\phi = 90°$, the C/Z element is moved out of the collection cone and the laser is again fired. Signal photons from the angular range of light collection are allowed to pass freely and be received by the collection optics in the same angular cone. The main laser beam 70 along the optical axis is blocked by beam blocking filter 92. Upon an additional 90° rotation, FIG. 5C-$\phi = 180°$, the C/Z element 41 reaches the zero signal position. All photons are blocked, thus simulating zero particulates in the sampling volume and a zero Z signal is developed at V1. The second signal position S2 is produced at $\phi = 270°$, as shown in FIG. 5D. At $\phi = 360°$, the process is repeated. The C/Z element is spun by a synchronous motor 82 on a common shaft 81 holding the C/Z element and the permanent magnet generator 86 which provides the $V_{100}$ pick-up voltage. Thus, two voltage signals, $v_\phi$ and $v_1$, are transmitted from the sensor unit along conductors 57 and 88 to control circuits of FIG. 3 which includes an analog board 93 which develops the C, Z and X signals and a digital board 94 which develops the gating pulse $V_g$ and diagnostic signals.

The digital board serves two functions: (1) timing the laser pulses for demultiplexing the $v_1$ signal and (2)

comparing the output signal and two system diagnostic signals from the analog to provide binary logic if the analog signals exceed pre-set bounds. Timing diagram of FIG. 4 illustrates the timing function of the digital board circuits. The voltage $v_\phi$ on line 88 is the initiating pulse for the system and originates when the cal/zero element 41 is near the calibration position, $\phi=0$. This pulse is received by a trigger stage 100 which produces a sharply rectangular pulse when its input trigger threshold is exceeded. This pulse then initiates four monostable multivibrators 101 a-d having increasingly long "on periods" shown by the waveforms labeled T1, T2 and T3 and T4. These pulses are in turn fed to an exclusive "or" circuit 102, the output of which is used to set an electronic single pole, four position switch 103 on analog board 93. At $t=T_1$, the logic circuitry produces gating pulse $v_g$ which is routed to the laser pulser board in the sensor unit through line 61. Additional gating pulses are produced at $t=T_2$, $T_3$ and $T_4$. The four equally spaced gating pulses fire trigger 60 which initiates monostable multivibrator 62 with $T_f=1$ millisecond. At $t=T_1+T_f$ the laser is "fired", producing in this case, a cal pulse at V1. At $t=T_2+T_f$, the laser is fired producing the $S_1$ pulse at V1. $A+T=T_3+T_f$, the zero signal is produced at V1 and the $S_2$ signal is produced at $T_3+T_f$. Thus, the laser fires at precisely known angular positions of the calibration element.

The V1 signal output of the sensor unit translated through line 57 is isolated by buffer amplifier 106 which is mechanically linked by range switch 107 to a variable gain 3-terminal amplifier 108. The output from amplifier 108 is filtered at 109 and stretched in stage 110 to develop the "fast" signal $V_5$. This signal is of considerable utility in diagnostics and measurements and is applied via line 111 to the input of electronic switch 103.

Noting that the calibration gating pulse is produced on the downward transition of $T_1$, it can be seen that the logic must provide a signal to the single pole, four position electronic switch which demultiplexes the $v_5$ signals. Thus, during the time interval $T_1 < t < T_2$ the calibration switch position is closed and the other positions are open to permit passage of electrical signals only through the CAL terminal output.

The signal is run through a range attenuator 104 and thence the negative (−) input of operational integrating amplifier 105, the positive (+) input of which is connected to the output of integrating amplifier 112. Amplifier 112 is connected to receive the Z terminal output of switch 103. The output of amplifier 105 is connected to an electronic summing junction 113 formed with reference source 114 whereupon the "running average voltage" corresponding to the cal signal is compared to a precision reference voltage. Any deviation from the reference constitutes an error voltage. This error voltage is then converted into a proportional current by the current source 115, which is used to set the gain of the variable gain element 108. The output of stage 105 is applied to amplifier 99 to develop the CAL signal C.

The importance of the functional position of the C/Z element and the associated circuitry can now be readily appreciated. All losses in transfer function from laser 50 through electronic switch 103 are automatically compensated by the feedback control system such that the overall transfer gain is constant. Should optical interfaces be contaminated by dust or impurities in the gas stream and result in an attenuation of either the laser beam, if it is passed through such interface, or by the signal photons in the preferred angular range, the control system will automatically and promptly increase the system gain to that prior to the contamination, i.e. to the gain originally set up with clean optics. After the C/Z element 41 has been rotated 90 degrees from the CAL position, the element 41 is out of the way of the preferred collection cone of signal photons scattered by particles in the sampling volume. These signal photons are detected and processed identically as was the calibration signal up to the electronic switch 103, whereupon they are fed directly to the positive (+) terminal of integrating operational amplifier 116. The positive (+) terminal of amplifier 116 is returned to the output of amplifier 112. The output of amplifier 116, is applied through an attenuating variable resistor element 117 to an OFF-SET adjustment network formed by resistors 118 and 119. The attenuated and offset signal is inverted and isolated by amplifier 120 to produce the mass concentration signal X. As far as the user of the instrumentation is concerned, this integrated or quasi-dc voltage is the most important output of the system.

The output is also valid for single large particle measurement. In the latter case, the signal from the S1, S2 output of switch 103 is also applied to a large particle compensation to circuit 121 to expand the response of the system to measurement of particulates having a mean diameter $d > 3$ $\mu$m. Considering the situation where a single particle occupies the sampling volume 42 when the C/Z element 41 is in a signal position, $\phi=90°$ or 270°, the light scattered into the collection optics is related to the particle size. Where $d > 3\lambda$, the voltage pulse V5 is proportional to $d^2$. Thus, the V5 height information contains particle size information which through pulse height analyzing means 121 is converted into a usable output signal applied to isolation amplifier 120. In cases where relatively few, but large particles ($d > 3\lambda$) are present with a relatively large number of small particles ($0.3\lambda < d < 3\lambda$), the large particles occupy the sampling volume one at a time, together with many of the smaller particles. For the smaller particles, the response is essentially to mass concentration. By subtracting the small particle signal from the large particle signal, a net voltage is generated for the relatively infrequent large particles corresponding to $d^2$. This net voltage may then be converted to $d^3$. The signal is weighted so that it is proportional to the contribution of large particles to the mass concentration. Finally, the weighted signal is added to the signal corresponding to the mass concentration of small particles using well known electronic techniques. The result is that the large particle compensation circuit 121 extends the upper range of response to true mass concentration.

Briefly, summarizing operation of the system, it can be seen that the $v\phi$ pulse from pick-up 87 initiates the cycle. Gate pulses developed in the digital board 94 both fires the laser 50 and sets the switch 103 for demultiplexing of the $v_5$ signals. The origin of these different signals is, of course, the four different positions of the cal/zero element as explained above.

The voltages $v_1$ transmitted from the sensor unit to the control/read-out unit by conductor 57 are processed by the analog board 93 as follows. First, the pulse is isolated from the transmission line by the buffer 106 following which the signal level is selected by the range attenuator 107. These signals are then fed into a variable gain control 108 which provides the control function for the feedback control loop for automatic compensation. The feedback control loop operates as follows. The C/Z element 41 injects a constant fraction of the laser power into the reception cone of the optical system. This fraction is the optical standard for the feedback loop. The signal, following processing by identical electronics, as for all other signals, is routed by switch 103 into attenuator 104 "ganged" with range switch 107, and then to an integrating amplifier 105 which converts the stretched pulses into quasi-dc levels.

The "open loop" output of the calibration channel amplifier represents a signal whose value is a measure of the transfer function of the entire electro-optical system from the laser power through the pulse stretcher. If the laser power reduces with age or increasing temperature or oil or dust contaminates the optical surfaces and reduces the transfer function, or if the detector or any electronic gains change, this signal wil be changed in proportion. Thus, it follows that, in "closed loop" operation, this signal is compared with a standard reference voltage 114 and fed back to the variable gain device 115 so that the system transfer gain, again from laser power to $v_5$, is held constant. The constant transfer gain established by the cal channel also holds for the other channels.

The zero signal Z is processed similarly and is converted via an integrating amplifier 112 into a DC voltage which is subtracted from both the cal and signal yields in amplifiers 105 and 116, respectively. [After the gain is adjusted, the pulses are shaped and stretched and fed to the electronic switch 103 whose conditions are established, as explained above, by the gating signals from digital board 94.]

The "fast" signal $v_5$ is also fed to a front panel (not shown) along with the gating voltage $v_g$ position voltage $V\phi$, C, Z and X signals, for possible particle size analysis experiments. The C, Z and X signals from amplifier 99, 112 and 120, respectively, are applied via lines 130, 131 and 132 to several threshold comparators to develop diagnostic and annunciator control voltages for monitoring operation of the system. Cal signal C is applied to comparator 133 whose output at line 134 represents a zero high signal. The zero signal Z is applied to comparator 135 whose output at line 136 represents a high calibration signal. The X signal is applied to two comparators 137 and 138, the latter preferably having a lower set point than the other. If the X signal exceeds the low threshold, the output of comparator 138 goes high and produces outputs at lines 139 and 140 after being passed through two adjustable time delays 141 and 142. Delay stage 141 introduces a delay in the order of $0 < T_5 < 50$ seconds. Delay stage 142 introduces a delay in the order of $50 < T_6 < 250$ seconds. If the X signal exceeds the upper threshold, an output signal is immediately generated on line 143. The comparator for the C and Z levels operate such that if zero or the calibration correction signal, which i inversely proportional to the electro-optical transfer function, exceed adjustable levels, the output signal goes from 0 to $+15$ volts. These logic signals are used to turn on a "MALFUNCTION" front panel light (not shown). User contacts may be provided for further annunciation or control.

Only the normal, compensating mode of operation has been described above. A switch 144 is provided on board 94 for manual set-up and diagnostics of the variable gain loop. Switch 144 permits 30 Hertz operation of the laser, via a 30 Hertz astable multivibrator 145, and selection of a preferred position for the electronic switch 103 via operation of switch 146 on board 93.

It should also be noted that $V\phi$ has been described as being generated by a permanent magnet pickup. Other means can be used for generating a $V\phi$ signal, such as, for example, a micro-switch in response to the position of shaft 81. Alternatively, rotor 85 may be slotted or provided with an aperture to permit rotor displacement to be monitored by means of a light source and detector. Obviously, various means may suggest themselves to those skilled in the art.

It should be noted that the signal data developed i.e., the C, Z and X signals are continuous and not interrupted. That is, the motor 82 turns sufficiently rapidly that the process is sampled at a high data rate integrated and subsequently presented as a continuous-noninterrupted-output analog voltage. This feature advantageously avoids interruption of data acquisition. The time response of the total system to step changes in mass concentration may be as fast as approximately 1/30 of a second. This is realized when the C/Z element turns at 15 revolutions per second and two signals are generated per revolution. Of course, other rotational speeds or even other means for introducing the calibration element may be envisioned, without alterning the validity of the concept, to increase or in some cases decrease the response time of the instrument.

Figure 6:
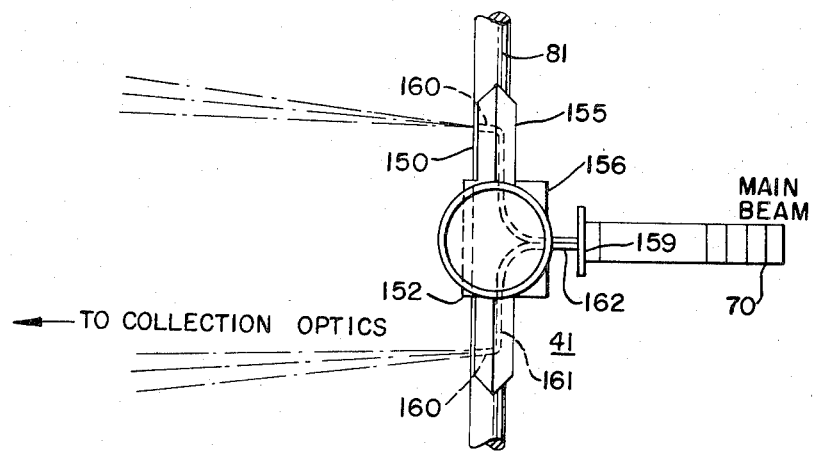
FIG. 6 is a fragmentary plan view of the calibration/zero element, with motor block removed illustrating in greater detail the relationship of the calibration/zero element to the path of radiation from the laser beam.
Figure 7:
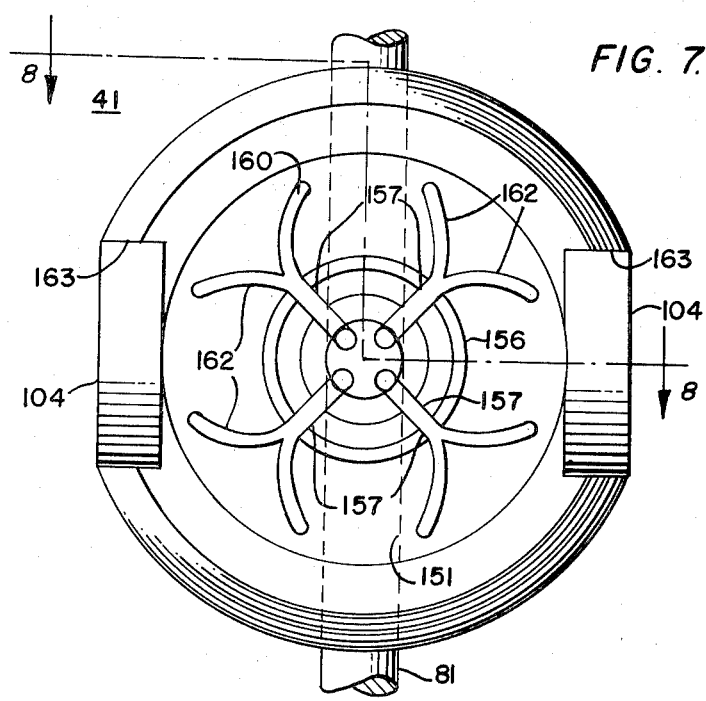
FIG. 7 is a detail elevational view of the calibration/zero element.
Figure 8:
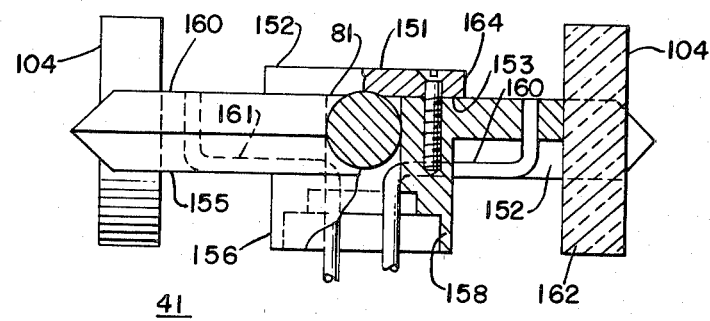
FIG. 8 is a view, partially in cross section, taken along lines 8—8 of FIG. 7.

The details of the physical structure of the cal/zero element 41 will now be described in connection with FIGS. 6 through 8. Element 41 comprises a substantially circular shaped A1 disc approximately two (2) inches in diameter, having a flat face 150 on one side thereof and a continuous groove 151 extending across the diameter thereof to receive shaft 81 of motor 82. The depth of groove 151 is such that the element may be readily clamped to shaft 81 by mounting plate 152 secured to face 150. To this end, a pair of threaded apertures 153 are provided which receive fastening bolts 164 which clamp mounting block 152 substantially flush with face 150 and tightly against the surface of shaft 81. The opposite face 155 of element 41 has extending therefrom a hub member 156 having four radial slots 157 arranged on diagonals which are offset 45° with respect to the axis of groove 151. Hub member 156 is counterbored as at 158 and adapted to receive therein a neutral density filter 159 which serves as a diffuser/attenuator. A plurality of transverse apertures 160 are provided inward of the periphery of element 41. Preferably, eight holes are provided and each hole is connected by means of a suitable radial channel or radial bore 161 to bore 158. Light striking the outward face of the diffuser is transmitted through the radial channels to the hole 160 by means of light tubes or fiber optics 162. To this end, 64 light tubes are provided arranged in bundles of eight. One end of each bundle is in contact with the back face of filter 159. The other end of each bundle terminates in an associated aperture 160 flush with one of the faces of element 41. Thus, for a forward scattering system, tubes 162 terminate flush with face 150 and redirect a predetermined fraction of light striking filter 159 to the collection optics at an angle corresponding to the angular range of high collection $\Delta\theta$ as shown in FIG. 6. For a backward scattering system, fiber optics 162 have their outermost ends bent in a reverse direction in apertures 160 such that the ends terminate flush with face 155 to redirect light from the direction from which it originates, i.e., counter to the arrow of incident light as shown in FIG. 6. The number of fiber optics could, of course, vary, depending on the selection of the filter. However, the arrangement should be such that the signal input is attenuated by a factor in the range of $10^{-2}$ to $10^{-8}$ and preferably $10^{-6}$. A pair of notches 163 are provided on opposite sides of the periphery of element 41 to support therein beam blocking filters 104 which serve to block the laser beam when the element 41 is rotated to the signal positions, $\phi = 90°$ and 270°, as shown in FIGS. 5B and 5D.

As should be apparent from FIG. 6, the axis of rotation of element 41 is perpendicular to the axis of incident light or laser beam 70. As the C/Z element rotates, typically synchronously, at, for example, 15 revolutions per second, it passes through four preferred spatial positions: calibration; signal 1; zero; and signal 2, corresponding to the positions shown in FIG. 5. At each position, corresponding calibration, signal 1, zero and signal 2, signals are generated and transmitted by the same electro-optical system. The signals are of a time-multiplexed nature. The calibration voltage is used to set the total system gain, within a wide dynamic range, so that loss of sensitivity is automatically and quickly compensated in either an analog or digital fashion. The output signal is not interruped and rapid response time to step changes in process conditions may be realized. Very low scattered signal levels, corresponding in the embodiment of FIG. 1 to very low mass concentration levels of aerosol, may be realized because of the noise suppression characteristics of the system and, the system's calibration is "tied" and traceable to the C/Z element which may readily be disengaged from shaft 81 and replaced with a C/Z element of known calibration while the doubtful element is checked against a standard.

The foregoing description should make it readily apparent that by the system and method of the present invention the variabilities in electro-optical measurements may be reduced, so that the principal advantages of such measurements may be more generally realized, with the confidence concomittant with improved precision and accuracy. Practically, the variability problem does not lie entirely within the electro-optical system itself. Another source of variability lies in the basic act of electro-optical transduction. For example, when measuring particulate characteristics via light scattering, it is well known that the amount of light scattered is sensitively dependent upon the particle size, shape, composition, location within the sampling volume, etc., etc. Thus in order to further minimize the variabilities of optical measurements, it is necessary to incorporate both the calibration/zero concept, disclosed above, with optimized, integrated, apparatus design. As an example, in the aforementioned U.S. Pat. No. 4,017,186 the particulate mass concentration of micron-sized particulates may be measured by backscattering means. However, this technique is applicable principally to particles whose index of refraction is real, such as for water, that is, the technique is not generally applicable and especially fails when the particles have a high index of absorption, as for iron oxides, metals, certain products of combustion, carbon, coal, etc. It is impossible to generally compensate such prior art apparatus for absorbing particles and rather, other electro-optical configurations must be utilized. Applicants have found that the forward scattering embodiment of the present invention is far superior, insofar as variabilities caused by particle composition effects are concerned.

Figure 9:
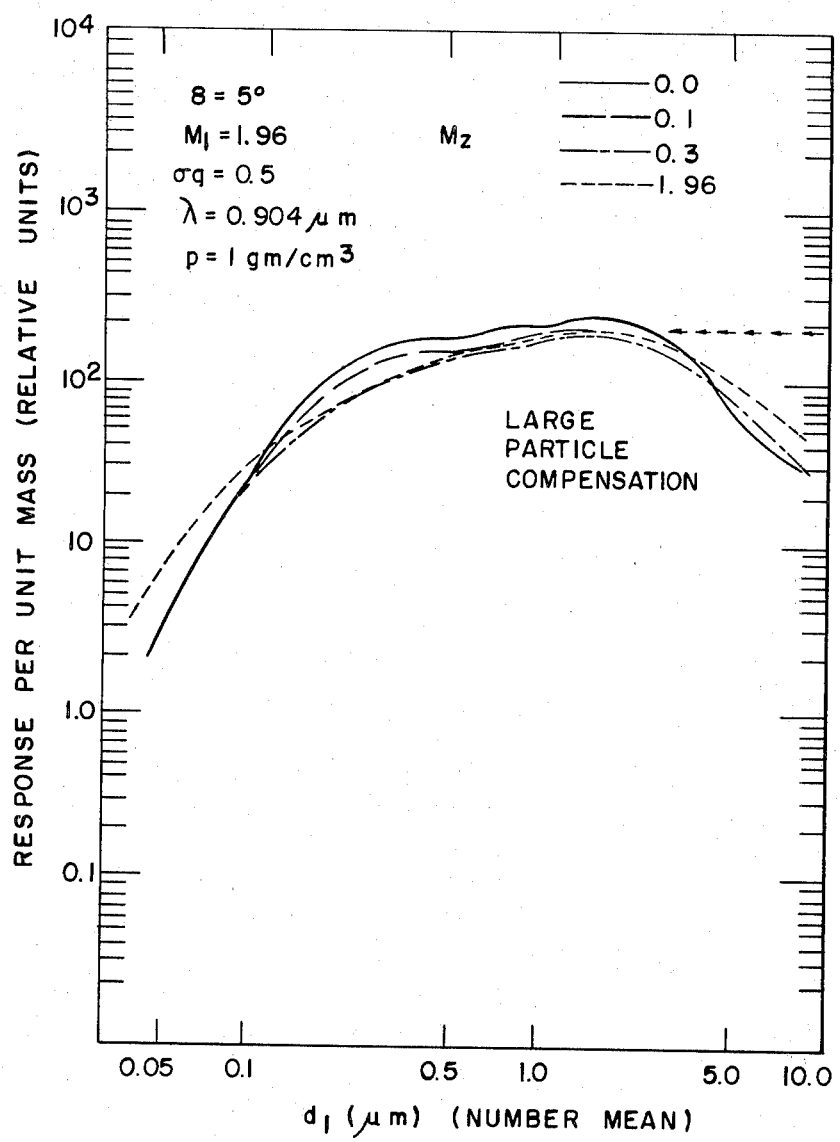
FIG. 9 is a response curve showing response per unit mass of absorbing particle distributions versus particle diameters for various absorption indices.

FIG. 9 demonstrates results which prove this assertion. Further reference may be made to the master's thesis of Arthur C. Miller, Jr., "Theoretical Modeling and Calibration for a Particulate mass Concentration Monitor," University of Tennessee, from which FIG. 9 was derived. The ordinate is proportional to particle mass concentration, for fixed mass density $\rho$ of the particle assumed, and the abscissa is the mean diameter of a log normal distribution of particle sizes. An ideal mass concentration instrument would show a horizontal straight line response, independent of particle size and composition. The subject invention, for particle mean diameters from roughly 0.3 to 3 micrometers, shows that the response is relatively constant with respect to particle size, when the illuminating wave length $\lambda$ is 0.9 micrometers. This phenomenon, approximate proportionality of system response to mass concentration for particle mean diameters from approximately $0.3\lambda$ to $3\lambda$, was recited in the aforementioned U.S. Pat. No. 4,017,186. However, as noted above, that recitation does not include absorbing particles, a more general case, and the backscattering instrumentation is found to be highly variable when compared to the present invention using forward scattering, wherein response is relatively independent of composition as shown by the four curves of FIG. 9 for different degrees of absorbing index of refraction, $m_2$. This invention exhibits the same $0.3\lambda$ to $3\lambda$ proportionality to mass concentration. Also, as shown in FIG. 9 for large particles $d > 3\lambda$, the upper range of the response may be extended as shown by the dotted curve by suitable compensation means.

While a particular embodiment of the invention has been described, it will be apparent to those skilled in the art that various modifications thereof may be made without departing from the true spirit and scope of the invention. Accordingly, it is intended by the appended claims to cover all such modifications which embody the inventive features as defined in the claims.

We claim:

1. A calibration/zero apparatus for an electro optical instrument comprising a plate element adapted to be rotatably positioned to intercept a beam of light, filter means having an inward face and an outward face, said inward face being disposed adjacent one side of said plate element in a plane oriented parallel with respect to the axis of rotation of said plate element and means in optical communication between said inward face and the other side of said plate element for transmitting a predetermined fraction of light striking said outward face of said filter means to one of said other sides of the plate element.

2. Apparatus as defined in claim 1 wherein said element includes a pair of diametrically disposed beam blocking optical elements supported at opposite peripheral surfaces of said plate and in a plane parallel to the axis of rotation of said element.

3. Apparatus as defined in claim 2 wherein said plate element includes a plurality of light tubes in optical communication between said inward and outward faces for directing said predetermined fraction of light to the other side of said plate element.

4. A calibrartion/zero element comrising a disc, having a first and a second flat face, a groove extending across one face for receiving means for supporting said disc for rotation about an axis lying in a plane parallel to said one face of the disc, a hub member extending from said second face, said hub member supporting a filter having a front and a back face and positioned to attenuate light striking its front face, a plurality of channels extending through said disc and optically connecting the back face of said filter and said first face of the disc such that light striking the front of the filter is transmitted through the disc.

5. A calibration/zero element as set forth in claim 4 further including a plurality of light tubes positioned in the channels, said light tubes having one end terminating at the back face of said filter and another end terminating flush with one of the faces of the disc.

6. A calibration/zero element as set forth in claim 5 wherein the other end of the light tube terminates with the first face.

7. A calibration/zero element as set forth in claim 5 wherein the other end of the light tube terminates with the second face such that light striking the filter is redirected to the direction from which it originates.

8. A calibration/zero element as set forth in claim 4 wherein said filter has an attenuation factor in a range of $10^{-2}$ to $10^{-8}$.

9. A calibration/zero element as set forth in claim 4 further including a pair of notches provided on opposite sides of the periphery of the disc and a light blocking filter supported in each notch.

10. A calibration/zero element comprising a disc, having a first and a second flat face, means for supporting said disc for rotation about an axis lying in a plane parallel to said first face of the disc, a filter supported to said second face and having a front and a back face and positioned to attenuate light striking its front face, a plurality of channels extending through said disc and optically connecting the back face of said filter and said first face of the disc such that light striking the front face of the filter is transmitted through the disc.

11. A calibration/zero element as set forth in claim 10 further including a plurality of light tubes positioned in the channels, said light tubes having one end terminating at the back face of said filter and another end terminating flush with one of the faces of the disc, in the other end of the light tube arranged to trerminate with the first face.

* * * * *